United States Patent
Al-Huwaider et al.

(10) Patent No.: US 11,680,484 B2
(45) Date of Patent: Jun. 20, 2023

(54) SYSTEM AND METHOD FOR MIXED WATER SALINITY CHARACTERIZATION

(71) Applicant: Saudi Arabian Oil Company, Dhahran (SA)

(72) Inventors: Mustafa A. Al-Huwaider, Dhahran (SA); Shouxiang Mark Ma, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 156 days.

(21) Appl. No.: 17/194,887

(22) Filed: Mar. 8, 2021

(65) Prior Publication Data

US 2022/0282618 A1    Sep. 8, 2022

(51) Int. Cl.
  *E21B 49/08*    (2006.01)
  *E21B 47/07*    (2012.01)
  (Continued)

(52) U.S. Cl.
  CPC .......... *E21B 49/0875* (2020.05); *E21B 47/07* (2020.05); *G01N 27/07* (2013.01); *G01N 27/10* (2013.01); *G01N 33/18* (2013.01)

(58) Field of Classification Search
  CPC .... E21B 49/0875; E21B 47/07; E21B 47/113; G01N 27/07; G01N 27/10; G01N 33/18; G01N 27/06; Y02A 90/30
  See application file for complete search history.

(56) References Cited

U.S. PATENT DOCUMENTS

| | | | |
|---|---|---|---|
| 4,754,839 A | | 7/1988 | Rathman |
| 4,982,383 A | * | 1/1991 | Sims ..................... E21B 47/107 73/861.18 |

(Continued)

FOREIGN PATENT DOCUMENTS

| | | |
|---|---|---|
| EP | 0866213 | 9/1998 |
| WO | WO 2007148269 | 12/2007 |

OTHER PUBLICATIONS

Mountsopris.com [online], "Q140-FTC-Fluid Temperature + Conductivity," Aug. 2014, retrieved on May 27, 22, retrieved from URL <https://mountsopris.com/q140-ftc-fluid-conductivity-and-temperature/>, 17 pages.

(Continued)

*Primary Examiner* — Blake Michener
*Assistant Examiner* — Yanick A Akaragwe
(74) *Attorney, Agent, or Firm* — Fish & Richardson P.C.

(57) ABSTRACT

Some implementations provide a tool assembly for monitoring reservoir water salinity and reservoir production performance at a borehole, the tool assembly comprising: a water salinity measuring probe that includes a pair of electrodes, wherein the water salinity measuring probe is mounted at a tip of the tool assembly and configured to measure a water conductivity between the pair of electrodes when the tool assembly is immersed inside the borehole; a spinner tool configured to measure a total flow rate at where the tool assembly is immersed inside the borehole, wherein the spinner tool is located above the water salinity measuring probe when the tool assembly is immersed inside the borehole; and a temperature probe configured to measure a temperature at where the tool assembly is immersed inside the borehole, wherein the temperature probe is located above the spinner tool when the tool assembly is immersed inside the borehole.

18 Claims, 10 Drawing Sheets

(51) Int. Cl.
*G01N 27/07* (2006.01)
*G01N 33/18* (2006.01)
*G01N 27/10* (2006.01)

(56) References Cited

U.S. PATENT DOCUMENTS

| | | | |
|---|---|---|---|
| 5,497,321 | A | 3/1996 | Ramakrishnan et al. |
| 6,061,634 | A | 5/2000 | Belani et al. |
| 6,176,129 | B1* | 1/2001 | Aguesse ................. E21B 47/01 73/152.29 |
| 6,227,045 | B1* | 5/2001 | Morse ....................... G01F 1/68 73/204.25 |
| 6,745,835 | B2 | 6/2004 | Fields |
| 8,265,874 | B2 | 9/2012 | Ma et al. |
| 10,208,582 | B2 | 2/2019 | Ma et al. |
| 10,247,849 | B2 | 4/2019 | Pfutzner et al. |
| 10,288,463 | B2 | 5/2019 | DiFoggio |
| 11,066,925 | B2 | 7/2021 | Ligneul et al. |
| 2003/0010135 | A1 | 1/2003 | Maxit et al. |
| 2008/0210420 | A1 | 9/2008 | Ramakrishnan et al. |
| 2015/0275661 | A1 | 10/2015 | Donzier et al. |
| 2018/0066501 | A1* | 3/2018 | Chidiac ................. G06F 30/20 |
| 2020/0208509 | A1* | 7/2020 | Chen ....................... E21B 47/12 |
| 2020/0355073 | A1 | 11/2020 | Maity et al. |
| 2022/0282618 | A1 | 9/2022 | Al-Huwaider et al. |

OTHER PUBLICATIONS

PCT International Search Report and Written Opinion in International Appln. No. PCT/US2022/019125, dated Jun. 15, 2022, 16 pages.

Ma et al., "Cased-hole reservoir saturation monitoring in mixed-salinity environments—A new integrated approach," SPE 92426 presented at the 14th SPE Middle East Oil & Gas Show and Conference, Bahrain, Mar. 12-15, 2005, 10 pages.

Ma et al., "Dynamic petrophysics—applications of time-lapse reservoir monitoring in Saudi Arabia," SPE 95882, presented at the 2005 SPE Annual Technical Conference and Exhibition, Dallas, Texas, Oct. 9-12, 2005, 8 pages.

Ma et al., "Resolving the mixed salinity challenges with a methodology developed from pulsed neutron capture gamma ray spectral measurements," SPE 170608, presented at the SPE Annual Technical Conference and Exhibition, Amsterdam, The Netherlands, Oct. 27-29, 2014, 12 pages.

* cited by examiner

SYSTEM AND METHOD FOR MIXED WATER SALINITY CHARACTERIZATION

TECHNICAL FIELD

This disclosure generally relates to mature reservoir dynamic description in the context of reservoir engineering and management.

BACKGROUND

Accurate reservoir characterization can be instrumental when monitoring a reservoir and optimizing its production (S. Ma, A. Hajari, O. Kelder, A. Muthana, A. Srivastava, & R. Ramamoorthy: "Dynamic petrophysics—applications of time-lapse reservoir monitoring in Saudi Arabia," SPE 95882, ATCE, 2005). For mature-reservoir description, accurate monitoring of oil saturation and its change with reservoir production can be challenging (S. Ma, A. Hajari, G. Berberian, & R. Ramamoorthy: "Cased-hole reservoir saturation monitoring in mixed salinity environments—a new integrated approach," SPE 92426, 2005 MOES).

SUMMARY

In one aspect, some implementations provide a tool assembly for monitoring reservoir water properties and reservoir production performance at a borehole, the tool assembly comprising: a water salinity measuring probe that includes a pair of electrodes, wherein the water salinity measuring probe is mounted at a tip of the tool assembly and configured to measure a water conductivity between the pair of electrodes when the tool assembly is immersed inside the borehole; a spinner tool configured to measure a total flow rate at where the tool assembly is immersed inside the borehole, wherein the spinner tool is located above the water salinity measuring probe when the tool assembly is immersed inside the borehole; and a temperature probe configured to measure a temperature at where the tool assembly is immersed inside the borehole, wherein the temperature probe is located above the spinner tool when the tool assembly is immersed inside the borehole.

Implementations may include one or more of the following features.

The pair of electrodes may be enclosed in a mesh coated with a superhydrophilic material capable of allowing water in and out of the water salinity measuring probe when the tool assembly is immersed inside the borehole. The water salinity measuring probe may be protected by a water-soluble shell comprising potassium chlorate or magnesium metallic sphere. The pair of electrodes of the water salinity measuring probe may be within a predefined distance of each other.

The tool assembly may further include a pressure probe configured to measure a pressure at where the tool assembly is immersed inside the borehole. The tool assembly may further include: one or more fluid holdup probes co-located with the spinner tool and configured to measure a water holdup, and thus infer an oil holdup, when the tool assembly is immersed inside the borehole. The tool assembly may additionally include: a caliper log capable of measuring a diameter of the borehole. The water salinity measuring probe, the spinner tool, the one or more fluid holdup probes, and the temperature probe may be coupled to a computer processor. The computer processor may be configured to: receive, from the tool assembly, data encoding measured water conductivity, measured total flow rate, measured water holdup, measured oil holdup, and measured temperature when the tool assembly is immersed inside the borehole; and based on the measured water conductivity and the measured temperature, calculate a flowing water salinity at where the tool assembly is immersed inside the borehole. The tool assembly may provide the measured water conductivity, the measured total flow rate, the measured water holdup, the measured oil holdup, and the measured temperature from two or more layers inside the borehole. The computer processor may be further configured to: receive, for the tool assembly, data encoding measured water conductivity, measured total flow rate, measured water holdup, measured oil holdup, and measured temperature from two or more layers inside the borehole; and based on the measured water conductivity, the measured total flow rate, the measured water holdup, the measured oil holdup, and the measured temperature from two or more layers inside the borehole, calculate a mixed flowing water salinity inside the borehole.

In another aspect, some implementations provide a method for monitoring reservoir production at a borehole, the method comprising: immersing a tool assembly inside the borehole, wherein the tool assembly includes a water salinity measuring probe, a spinner tool, and a temperature probe, and wherein the water salinity measuring probe includes a pair of electrodes; measuring a water conductivity between a pair of electrodes of a water salinity measuring probe when the tool assembly is immersed inside the borehole; measuring, using the spinner tool of the tool assembly, a total flow rate at where the tool assembly is immersed inside the borehole; and measuring, using the temperature probe of the tool assembly, a temperature at where the tool assembly is immersed inside the borehole.

Implementations may include one or more of the following features.

The method may further include: operating the pair of electrodes located inside a mesh coated with a superhydrophilic material such that water is allowed in and out of the water salinity measuring probe. The method may further include: enclosing the water salinity measuring probe with a water-soluble shell comprising potassium chlorate or magnesium metallic sphere. The method may further include: mounting the water salinity measuring probe at a tip of the spinner tool.

The method may further include: measuring, using a pressure probe, a pressure at where the tool assembly is immersed inside the borehole. The method may further include: measuring, using one or more fluid holdup probes, a water holdup and an oil holdup when the tool assembly is immersed inside the borehole. The method may further include: receiving, from the tool assembly, data encoding measured water conductivity, measured total flow rate, measured water holdup, measured oil holdup, and measured temperature when the tool assembly is immersed inside the borehole; and based on the measured water conductivity and the measured temperature, calculating a flowing water salinity at where the tool assembly is immersed inside the borehole. The method may further include: obtaining the measured water conductivity, the measured total flow rate, the measured water holdup, the measured oil holdup, and the measured temperature from two or more layers inside the borehole. The method may further include: receiving, for the tool assembly, data encoding measured water conductivity, measured total flow rate, measured water holdup, measured oil holdup, and measured temperature from two or more layers inside the borehole; and based on the measured water conductivity, the measured total flow rate, the measured water holdup, the measured oil holdup, and the measured temperature from two or more layers inside the borehole, calculating a mixed flowing water salinity inside the borehole.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

DESCRIPTION OF DRAWINGS

Like reference numbers and designations in the various drawings indicate like elements.

DETAILED DESCRIPTION

Figure 1:
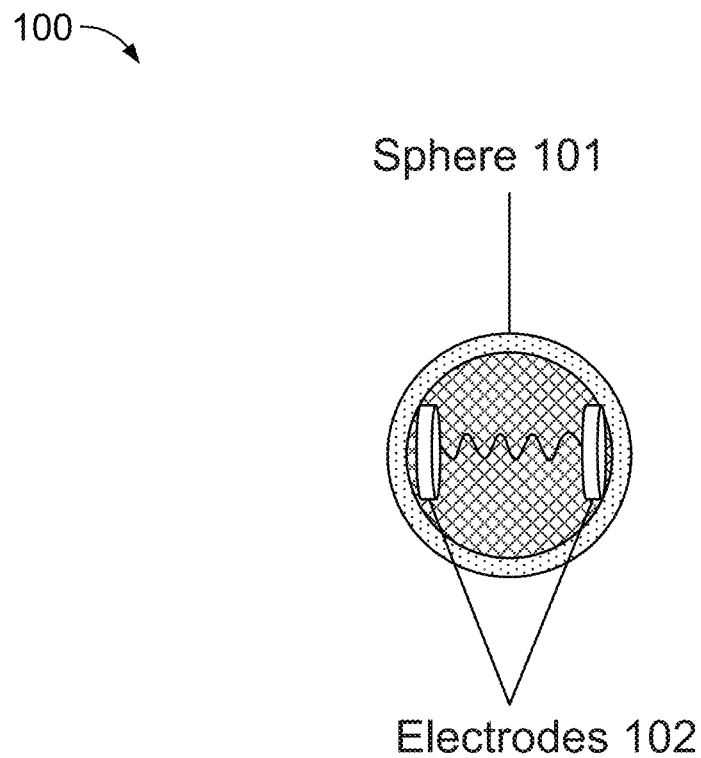
FIG. 1 shows an example of a water salinity measuring probe according to an implementation of the present disclosure.

Accurate reservoir characterization can be instrumental in managing a reservoir and optimizing its production. For mature-reservoir description, accurate monitoring oil saturation can be a major challenge. Traditional methods for dynamic saturation monitoring generally use resistivity tools, pulsed neutron capture (sigma) tools or pulsed neutron inelastic spectral carbon-oxygen (CO) tools. Each has its limitations (S. Ma, A. Al-Hajari, & K. Husain: Expert system for selecting fit-for-purpose technologies and wells for reservoir saturation monitoring, U.S. Pat. No. 8,265,874, 11 Sep. 2012). For example, carbon-oxygen (CO) has a shallow depth of investigation (DOI), which can severely limit the range of applicable monitoring. Resistivity tools can have a much deeper DOI but the operation can depend on formation water salinity. Conventional reservoir development generally uses injected water to maintain reservoir pressure. However, characterizing formation water salinity in an operating field under-going water injection is an industry-wide challenge, because the injected water will mix with reservoir connate water resulting in a mixed salinity issue. To obtain formation salinity, current methods generally extract physical samples and then send the collected fluid to specialized labs for physical and chemical analysis (S. Ma, A. Hajari, G. Berberian, & R. Ramamoorthy: "Cased-hole reservoir saturation monitoring in mixed salinity environments—a new integrated approach," SPE 92426), although attempts to extract formation water salinity from continuous logs is on-going (S. Ma, H. Pfuzner, A. Hajari, N. Musharfi, P. Saldungaray, and M. Hisham: "Resolving the mixed salinity challenges with a methodology developed from pulsed neutron capture gamma ray spectral measurements," SPE 170608, SPE ATCE 2014. S. Ma, Musharfi, N., Saldungaray, P., and Pfutzner, H.: Formation water salinity from borehole measurements, U.S. Pat. No. 10,208,582, 19 Feb. 2019. H. G. Pfutzner, J. A. Grau, R. E. Plasek, R. Ramamoorthy, and S. Ma: Method and apparatus for measuring formation water salinity in a borehole, U.S. Pat. No. 10,247,849, 2 Apr. 2019).

In the present disclosure, system and method are developed to directly measure, in-situ, flowing water salinity from electric current resistivity or conductivity. Some implementations employ two electrodes inside a sphere of non-conductive oil repellant mesh (coated with, for example, superhydrophilic material to minimize oil influence). The implementations are capable of measuring in situ produced fluid salinity and flow rate at various layers. Based on the multiple measurements taken on-site, the implementations can monitor mixed water salinity periodically during routine operations in a production well.

The terminology used in the present disclosure includes the following terms.

The term "machine learning analytics" refers to the use of machine learning and applied statistics to predict unknown conditions based on the available data. Two general areas that fall under machine learning analytics are classification and regression. While classification refers to the prediction of categorical values, regression connotes the prediction of continuous numerical values. One machine learning implementation is also known as "supervised learning" where the "correct" target or y values are available. For illustration, the goal of some implementations is to learn from the available data to predict the unknown values with some defined error metrics. In supervised learning, for example, there are a set of known predictors (features) $x_1, x_2, \ldots, x_m$ which are known to the system as well as the target values $y_1, y_2, \ldots, y_n$, which are to be interred. The system's objective is to train a machine learning model to predict new target values $y_1, y_2, \ldots, y_n$ by observing new features.

The implementations can employ a variety of machine learning algorithms. For classification, examples of prediction algorithms can include, logistic regression, decision trees, nearest neighbor, support vector machines, K-means clustering, boosting, and neural networks. For regression, examples of predication algorithms can include least squares regression, Lasso, and others. The performance of an algorithm can depend on a number factors, such as the selected set of features, training/validation method and hyper-parameters tuning. As such, machine learning analytics can manifest as an iterative approach of knowledge finding that includes trial and error. An iterative approach can iteratively modify data preprocessing and model parameters until the result achieves the desired properties.

FIG. 1 shows an example of a water salinity measuring probe 100 including electrodes 102 and sphere 101. In this example, sphere 101 is a non-conductive oil repellent mesh. In some cases, sphere 101 is coated with superhydrophilic material to minimize oil influence. For example, the superhydrophilic material coating the mesh can provide a membrane that is highly water wet to repel oil away from the sphere while allowing water in and out of the probe, with optimized mesh opening sizes. Electrodes 102 can be arranged on two poles of the sphere and, once energized, can provide an electric field between the pair of electrodes to measure conductivity, or resistivity.

Figure 2:
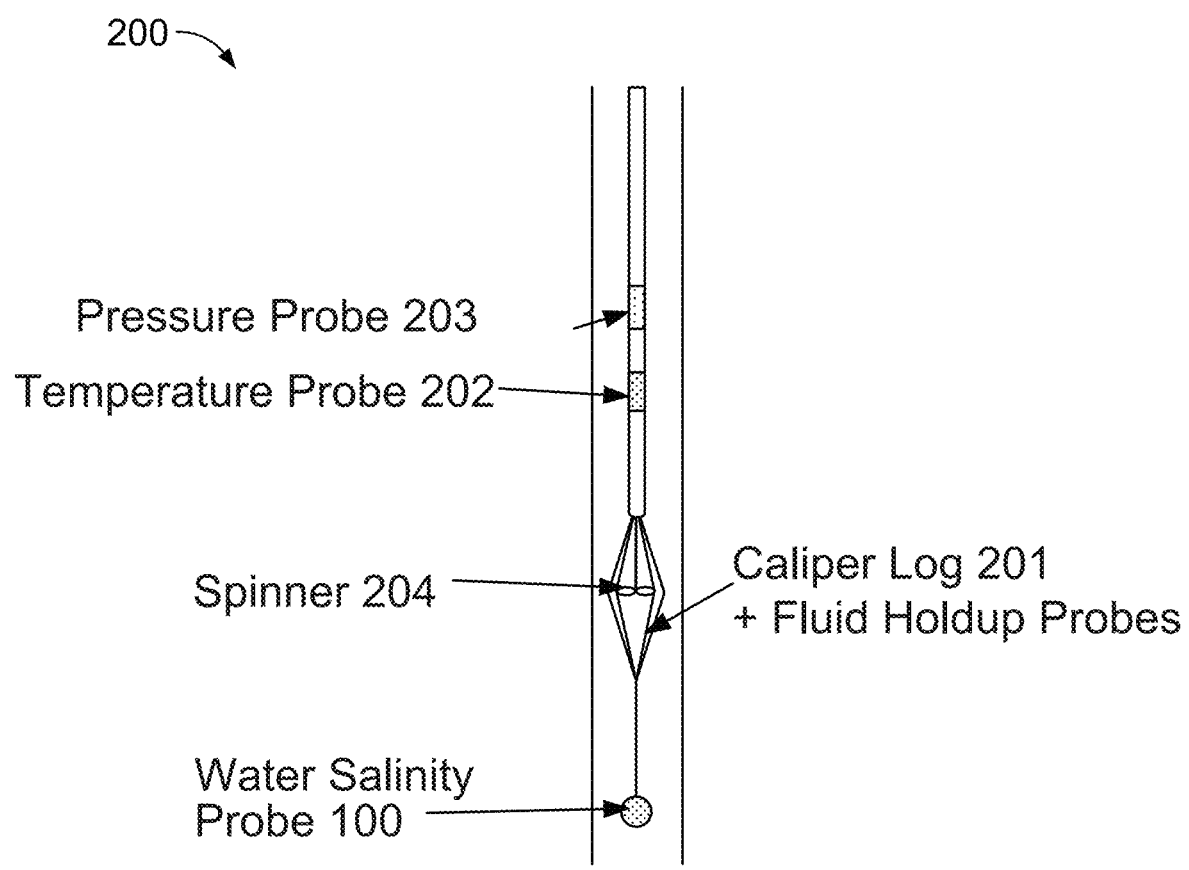
FIG. 2 is an example of a water salinity measuring probe as part of a production log setup according to an implementation of the present disclosure.

Referring to FIG. 2, in some implementations, water salinity measuring probe 100 can be mounted at the tip of a production tool inside a shaft of a borehole. The tool assembly includes a temperature probe 202, a pressure probe 203, a spinner 204, caliper tool and fluids holdup probe 201, and the water salinity measuring probe 100. As illustrated, the spinner 204, caliper and fluids holdup probe 201 can profile and quantify multiphase flow patterns including relatively complex flow patterns. In this configuration, the tool assembly can allow for simultaneous exposure to fluid parameters including temperature, pressure, total and phase flow rates, and water salinity. In comparison with other downhole tools that only sample points in the wellbore, the tool assembly can continuously measure formation salinity.

Figure 3:
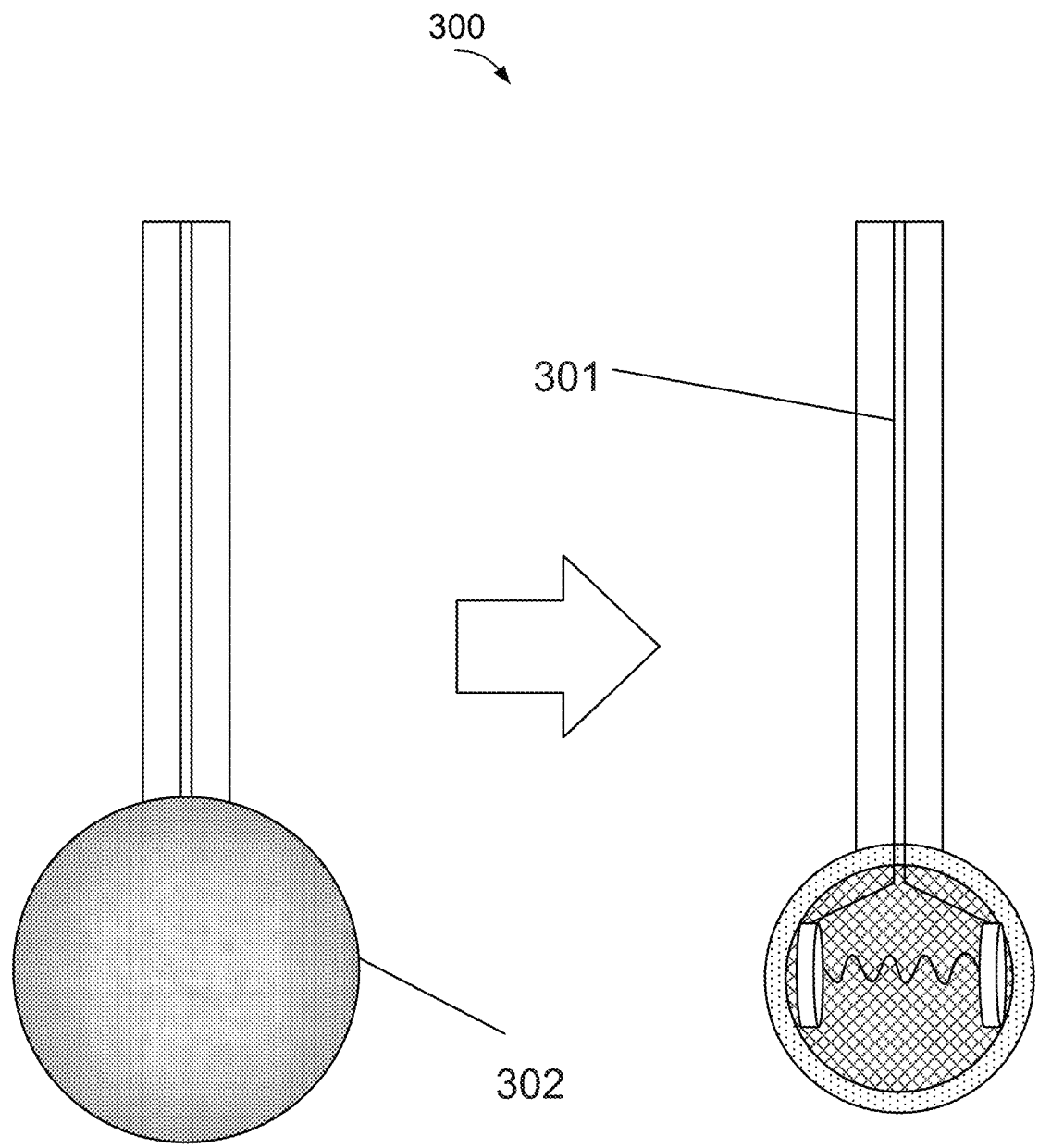
FIG. 3 is an example of a water salinity measuring probe protected by a water soluble shell or magnesium metallic sphere according to an implementation of the present disclosure.
Figure 4:
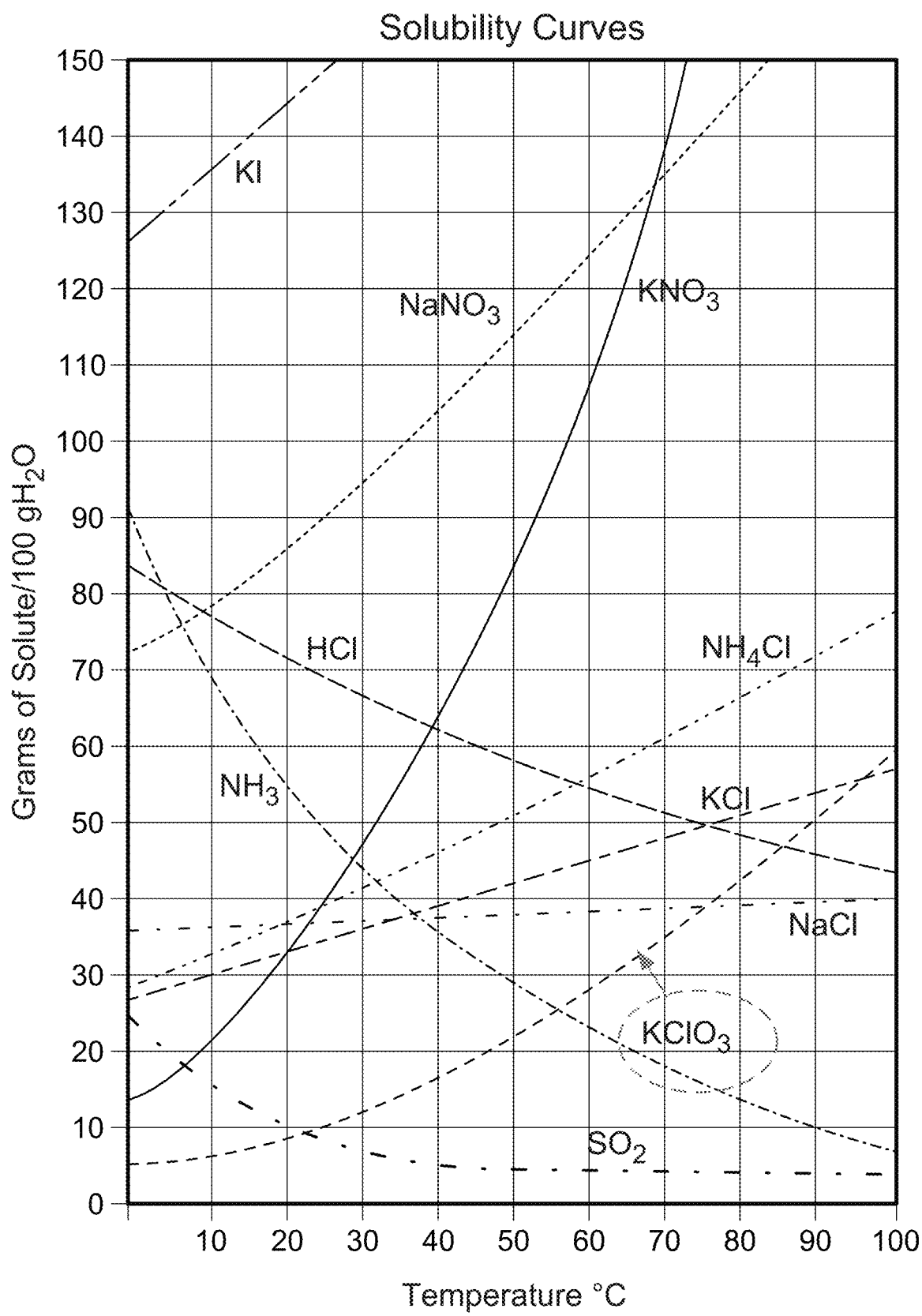
FIG. 4 is an example of examples of solubility curves of different salt compounds according to an implementation of the present disclosure.

Further referring to FIG. 3, diagram 300 shows an example of a tool assembly, configuration in which wire 301 connects to water salinity measuring probe 100. The example also demonstrates that, while running the tool assembly in borehole, the water salinity measuring probe 100 is protected by a water-soluble shell or magnesium metal 302. The shell itself may also be coated with superhydrophilic material to protect the probe from contamination by oil due to long exposure to oil column, especially if crude oil is waxy or contains high asphaltene content. Some implementations may use a protective substance that is stable at surface conditions but highly/moderately water-soluble at reservoir conditions or highly water-reactive metal at reservoir conditions. Further referring to FIG. 4, an example of such substance is potassium chlorate $KClO_3$, which is highly water-soluble at high downhole temperatures or magnesium which is highly, reactive with water at high downhole temperatures. After completing each logging run, the tip of the tool assembly can be cleaned using solvents and then re-coated with water-soluble shell or magnesium metallic sphere for the next logging run.

Figure 5:
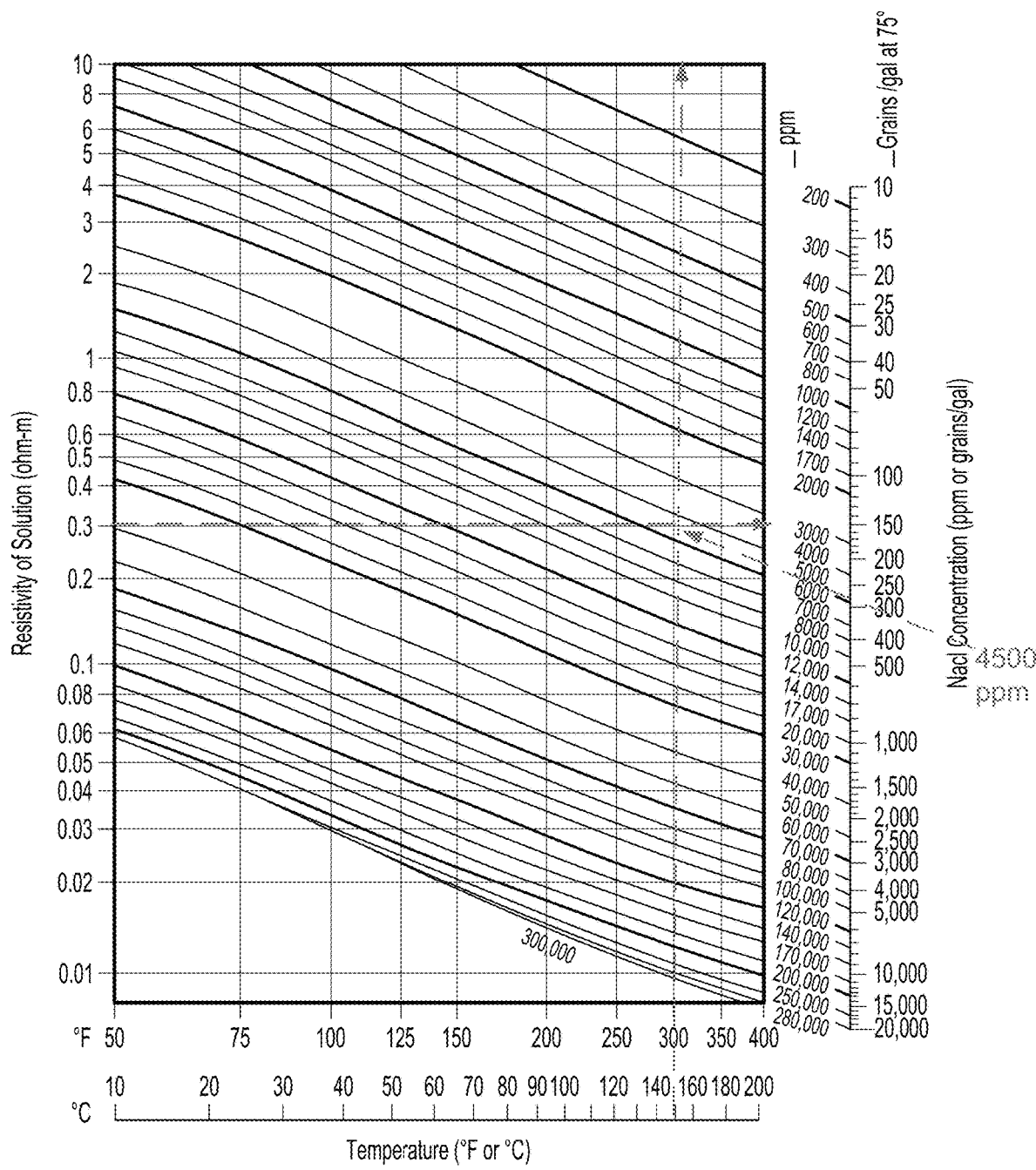
FIG. 5 is a chart used in the oil industry and some implementations of the present disclosure to estimate water resistivity from NaCl concentration and temperature.

Based on a relationship between conductivity and water salinity, various implementations can convert the measured conductivity values, as measured by sensors in FIGS. 1 and 3, to water salinity. An example of a chart for converting borehole water resistivity or conductivity to water salinity (C) is presented in FIG. 5. Based on this example chart, water salinity values can be determined from the measured water conductivity or resistivity, along with the temperature measurements. For example, if the resistivity measurement from the water salinity measuring probe is 0.3 ohm-m and the borehole temperature is 160° C., then the water salinity is around 4500 ppm or 4.5 kppm, as illustrated in FIG. 5.

Based on the measured borehole water salinity, various implementations may perform inversion to determine formation water salinity for reservoir management and reservoir saturation monitoring. Further referring to FIGS. 6A and 6B, various implementations can perform inversion to extract formation water salinity based on borehole measurements of flow profile (e.g., Qi, the flow rate of water or oil) in addition to borehole water salinity profile.

Figure 6A:
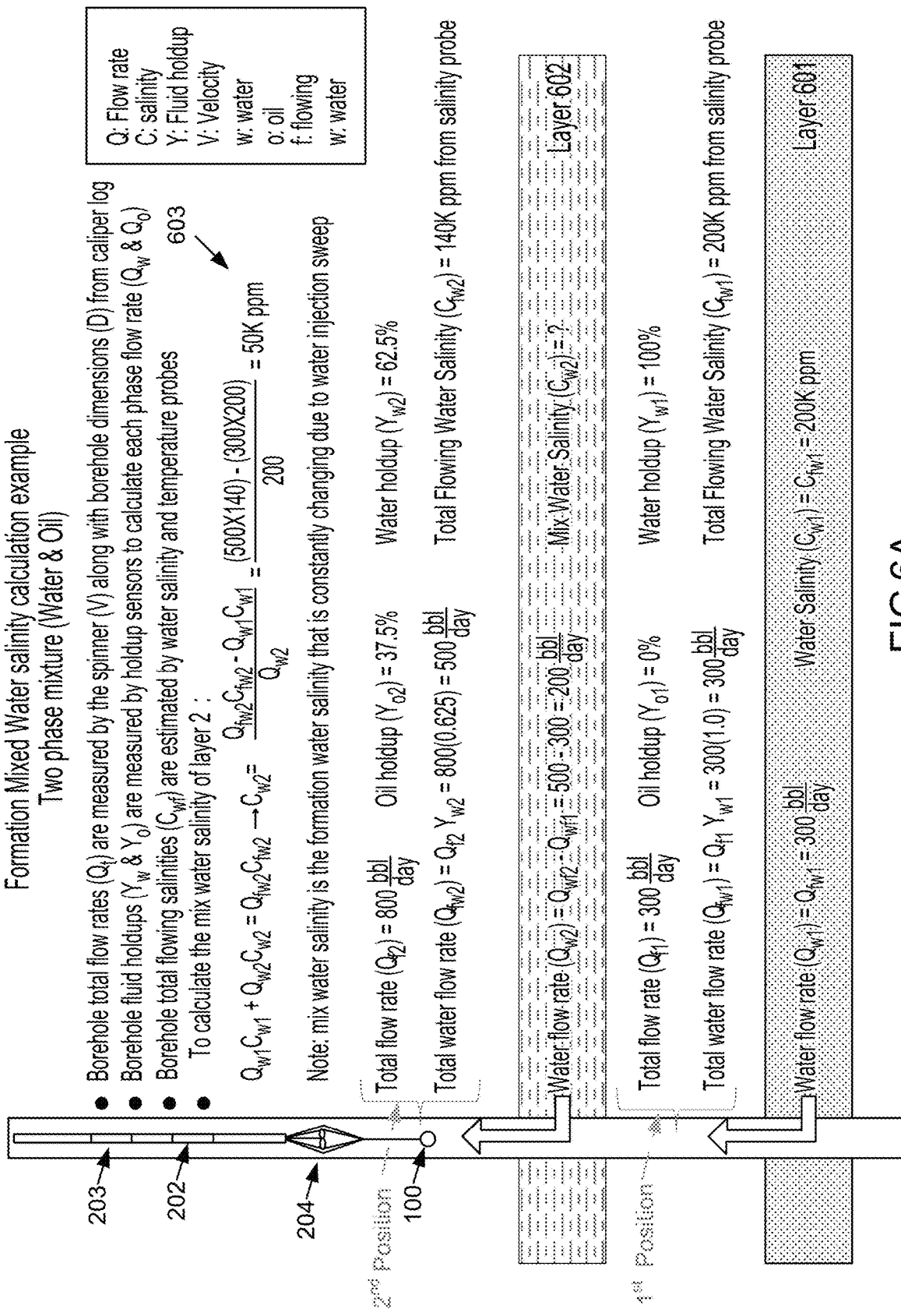
FIGS. 6A-6B show examples of mixed formation water salinity calculation according to some implementations of the present disclosure.

As illustrated in the two phase mixture example of FIG. 6A, the tool assembly is lowered into a shaft to perform in-situ measurement using water salinity measuring probe 100, spinner and fluids holdup probe 204, caliper tool 201, pressure probe 203, and temperature probe 202. As illustrated, the tool assembly encounters two layers, namely layer 601 and layer 602. Layer 601 is lower than layer 602. Both layers exhibit water outflow. As illustrated, spinner tool 204 measures flow velocity V while caliper tool 201 measures bore diameter D. Total flow rate Q is calculated from V and D. Additionally, holdup sensors can measure borehole fluid holdups for water ($Y_w$) thus oil ($Y_o$) for that $Y_w+Y_o=1$. Based on these measurements (Q and $Y_w$) and estimated fluids slippage, the flow rate for each phase (water and oil) can be calculated. For example, at the position between layer 601 and layer 602, the borehole total flow rate $Q_{f1}$ is observed at 300 bbl/day. Oil holdup $Y_{o1}$ is measured at 0% thus water holdup $Y_{w1}$ is 100%. The total water flow rate at layer 601 is thus: $Q_{fw1}=Q_{f1}\cdot Y_{w1}=300\times 1.0=300$ bbl/day. In the meantime, at the position of layer 601, the total borehole flowing water salinity is determined to be 200 k ppm based on conductivity measurement from water salinity probe 100 and temperature reading from temperature probe 202. In this example, at the position above layer 602, the total flow rate $Q_{f2}$ is observed at 800 bbl/day. Oil holdup $Y_{o2}$ is measured at 37.5% thus water holdup $Y_{w2}$ is 62.5%. The total water flow rate at layer 602 is thus: $Q_{fw2}=Q_{f2}\cdot Y_{w2}=800\times 0.625=500$ bbl/day (assuming slippage between oil and water can be neglected), and water production rate from layer 602 is 200 bbl/day ($Q_{w2}=Q_{fw2}-Q_{fw1}$). In the meantime, for layer 602, the total borehole flowing water salinity is determined to be 140 k ppm based on conductivity measurement from water salinity probe 100 and temperature reading from temperature probe 202. As illustrated in 603, the mixed formation water salinity in layer 602 can be determined as:

$$C_{w2} = \frac{Q_{fw2}C_{fw2} - Q_{w1}C_{w1}}{Q_{w2}} = \frac{(500\times 140)-(300\times 200)}{200} = 50k \text{ ppm} \quad (1)$$

Figure 6B:
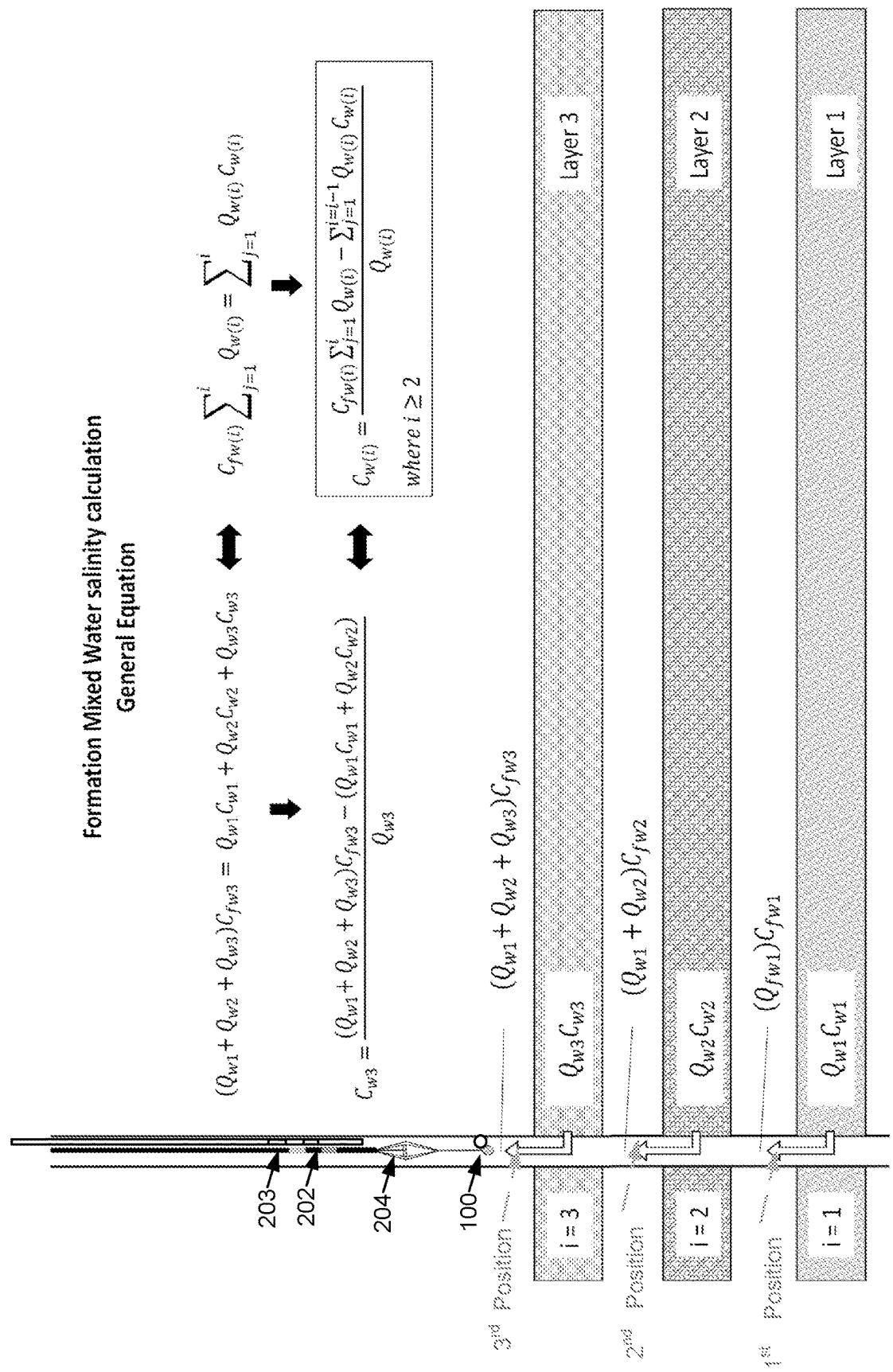

An example of three layers (namely, layers 1, 2, and 3) is shown in FIG. 6B. In this example involving; three layers, the mixed water salinity at layer 613 can be determined as:

$$C_{w3} = \frac{(Q_{w1}+Q_{w2}+Q_{w3})C_{fw3} - (Q_{w1}C_{w1}+Q_{w2}C_{w2})}{Q_{w3}} \quad (2)$$

In a more generalized example involving multiple layers, the mixed water salinity at the top layer can be determined as:

$$C_{w(i)} = \frac{C_{fw(i)}\left(\sum_{j=1}^{i}Q_{w(j)} - \sum_{j=1}^{i-1}Q_{w(j)}C_{w(j)}\right)}{Q_{w(i)}} \quad (3)$$

Figure 7:
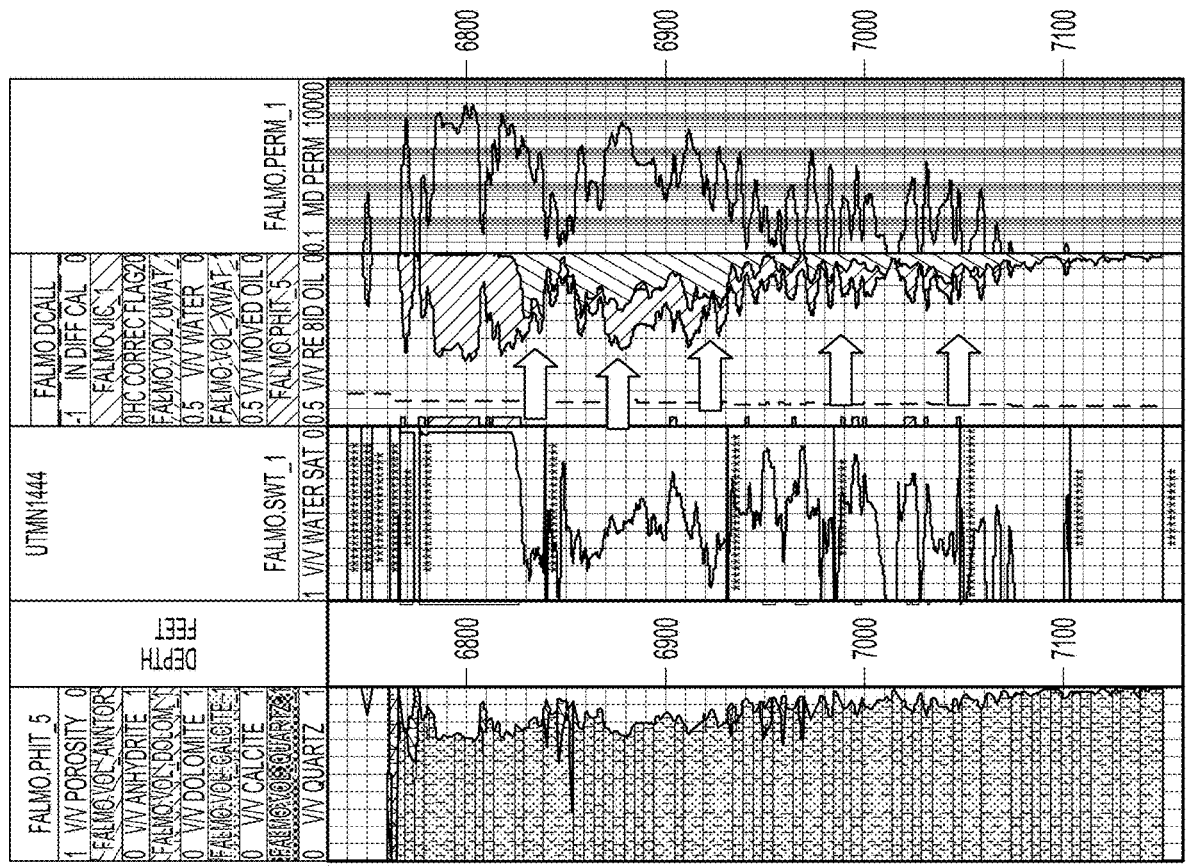
FIG. 7 shows an example acquiring formation water salinity using samples taken from bottom holes as compared to implementations of the present disclosure.
Figure 7:
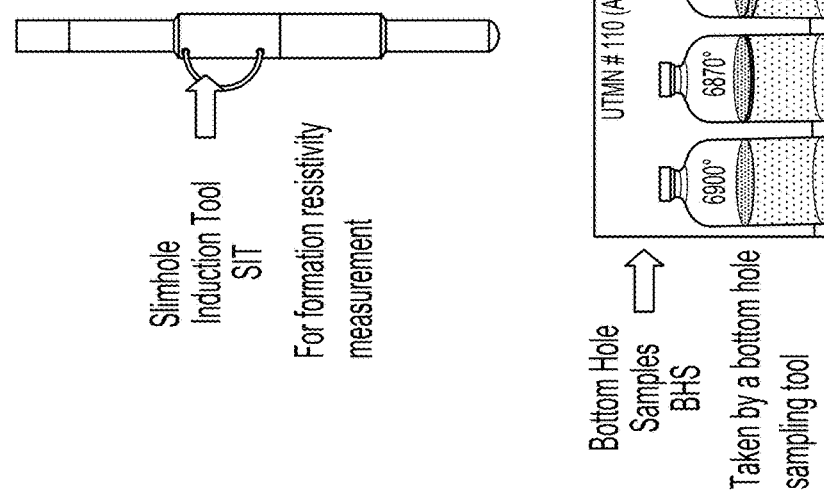

With a DOI (depth of investigation) of about 90 inches, resistivity can provide a much deeper measurement comparing to the typical pulsed neutron (PN) and carbon oxygen (CO) measurements which can only penetrate around 6 inches or so. For this reason alone, implementations described in the present disclosure is advantageous for monitoring reservoir saturation, especially when borehole and near-wellbore effect are significant, such as washout borehole, borehole fluid invasion or re-invasion, since the deep measurement of resistivity is much less sensitive to borehole and near well effects (A. Sunbul, S. Ma, A. Hajari, A. Srivastava, & R. Ramamoorthy: "Quantifying remaining oil by use of slim-hole resistivity measurement in mixed salinity environments—a pilot field test," SPE 97489). Moreover, implementations described by the present disclosure can continuously measure formation water salinity. Specifically, the implementations can measure flowing borehole water salinity based on real-time electric current resistivity or conductivity measurement and temperature measurement. The resistivity/conductivity measurement is based on measurement between two electrodes inside a sphere of non-conductive oil repellant mesh. The in-situ measurement of flowing water can improve the accuracy of resistivity log interpretation for formation water saturation. In comparison, conventional practice generally acquires formation water salinity by taking bottom hole samples. Conventional technology may use a formation testing and sampling (FTS) tool with large tool diameter during an expensive rig operation, which may be applicable in newly drilled wells with a good mud cake sealing. Conventional technology may also use slimhole bottom sampler (BHS) which can only collect limited downhole samples per run. With BHS, samples are often taken with slick line blindly, in which case the type of samples can be unknown during sampling. As illustrated in FIG. 7, when using a slimhole induction tool (SIT) to extract bottom hole samples (BHS) from a wellbore, the samples may be sent to a laboratory for analysis. The results from the analysis may then be correlated. As such, conventional technology can only, operate on discrete samples and the analysis may not provide the advantageous interpretation of formation water salinity in-situ. Indeed, unlike FTS samples which can be taken at a specific depth from a targeted formation layer, BHS samples, if taken under flowing conditions, are a mixture of fluids flowing from the sampling depth and below. As such, without proper inversion like Eq. 3, the result is not representative of the target reservoir layer which is needed for resistivity based reservoir saturation calculation. Conventional technology may also use wellhead samples (WHS). While WHS can be the simplest and cheapest way to collect a well flowing sample, the samples collected are mixtures of all flowing contribution intervals, thus are not representative of the target reservoir fluid properties.

Figure 8:
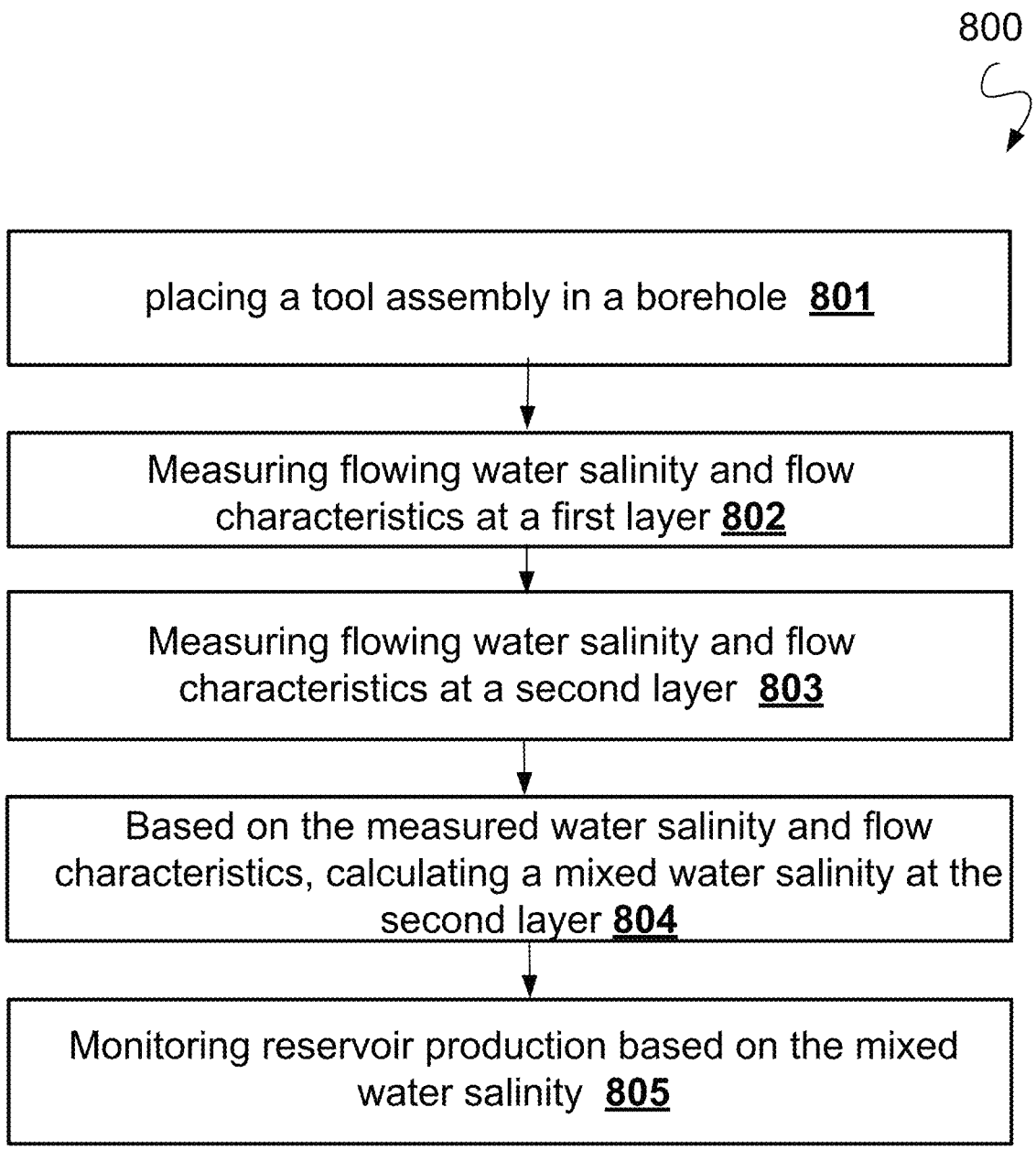
FIG. 8 is an example of a flow chart according to an implementation of the present disclosure.

As illustrated by the flow chart 800 of FIG. 8, an implementation may start with placing a tool assembly inside a borehole (801). As described in more detail in FIGS. 1-3, an example of a tool assembly can include a water conductivity measuring probe, a spinner, one or more fluid holdup probe, a temperature probe, and a pressure probe. In some implementations, the water conductivity measuring probe includes a pair of electrodes arranged to face each other inside a mesh coated with a superhydrophillic material. For example, the superhydrophillic material coating the mesh can provide a membrane that is highly water wet to repel oil away from the sphere while allowing water in and out of the probe.

Next, the implementations may measure flowing borehole water salinity and flow characteristics between a first and a second layer when the tool assembly is immersed in the borehole (802). For example, using the water salinity measuring probe, implementations can measure water conductivity between the pair of electrodes. Based on the measured water conductivity, along with measured temperature, implementations can calculate a water salinity value. Coupled with additionally measured flow characteristics, including flow rate, water holdup thus oil holdup, the implementations may calculate flowing water salinity for the first layer.

Thereafter, the implementations may measure flowing water salinity and flow characteristics above a second layer when the tool assembly is immersed in the borehole (803). In some cases, as illustrated in, for example, FIGS. 6A and 6B, layer 2 is higher than layer 1. In these cases implementations can measure water conductivity between the pair of electrodes of the water salinity measuring probe. Based on the measured water conductivity, along with measured temperature, implementations can calculate a water salinity value. Coupled with additionally, measured flow characteristics, including flow rate, water holdup and oil holdup, the implementations may calculate flowing water salinity for the second layer.

Figure 9:
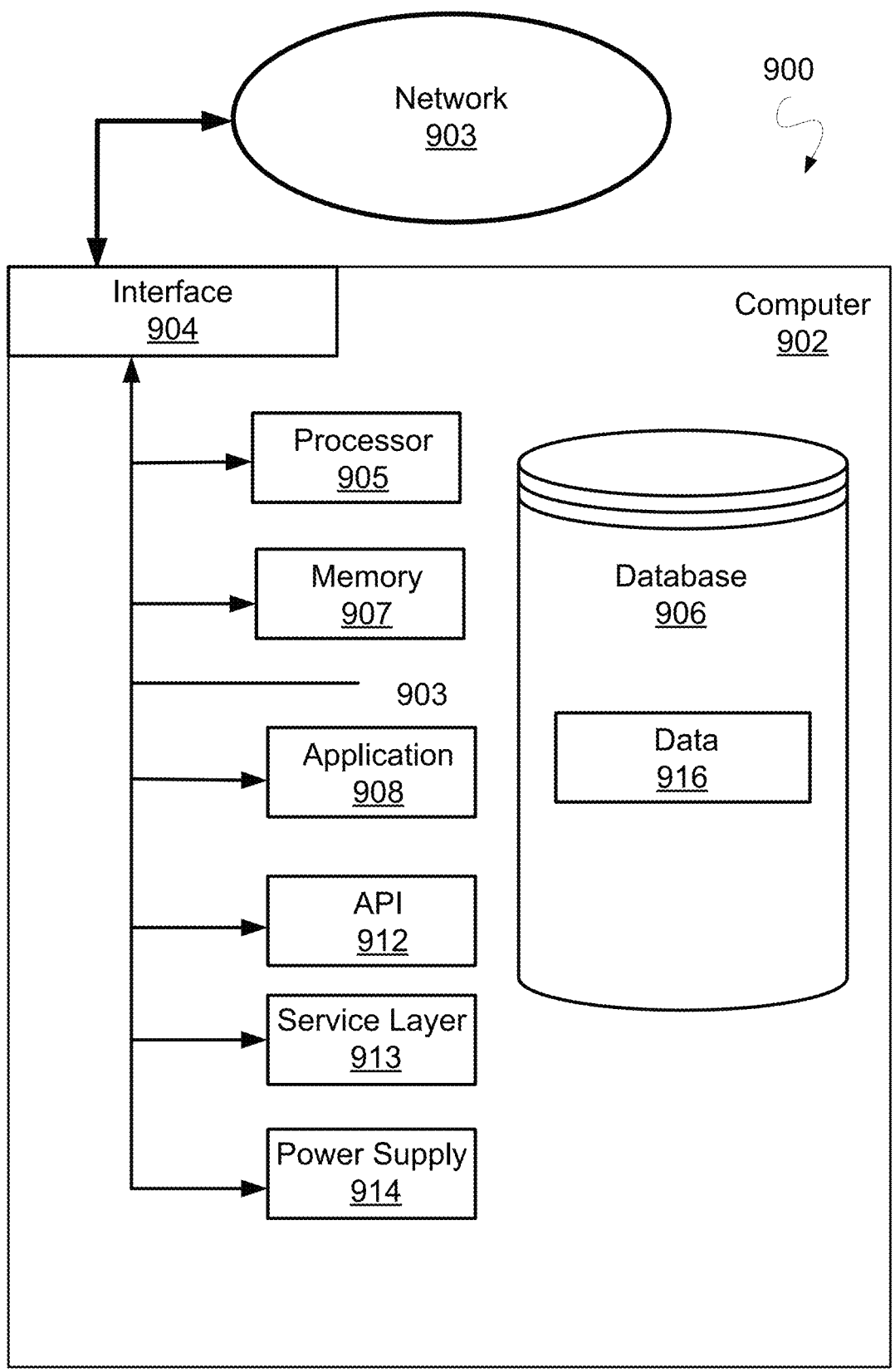
FIG. 9 is a block diagram illustrating an example of a computer system used to provide computational functionalities associated with described algorithms, methods, functions, processes, flows, and procedures, according to an implementation of the present disclosure.

Based on the measured water salinity and flow characteristics from the two layers, implementations may calculate a mixed water salinity, for example, at the second layer (804), as illustrated in FIGS. 6A-6B. Implementations may then continually monitor reservoir production based on the mixed water salinity (805). For example, implementations may apply machine learning analytics to predict reservoir oil production and water injection performances based on monitored information, including monitored water salinity, FIG. 9 is a block diagram illustrating an example of a computer system 900 used to provide computational functionalities associated with described algorithms, methods, functions, processes, flows, and procedures, according to an implementation of the present disclosure. The illustrated computer 902 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 902 can comprise a computer that includes an input device, such as a keypad, keyboard, touch screen, another input device, or a combination of input devices that can accept user information, and an output device that conveys information associated with the operation of the computer 902, including digital data, visual, audio, another type of information, or a combination of types of information, on a graphical-type user interface (UI) (or GUI) or other UI.

The computer 902 can serve in a role in a computer system as a client, network component, a server, a database or another persistency, another role, or a combination of roles for performing the subject matter described in the present disclosure. The illustrated computer 902 is communicably coupled with a network 903. In some implementations, one or more components of the computer 902 can be configured to operate within an environment, including cloud-computing-based, local, global, another environment, or a combination of environments.

The computer 902 is an electronic computing device operable to receive, transmit, process, store, or manage data and information associated with the described subject matter. According to some implementations, the computer 902 can also include or be communicably coupled with a server, including an application server, e-mail server, web server, caching server, streaming data server, another server, or a combination of servers.

The computer 902 can receive requests over network 903 (for example, from a client software application executing on another computer 902) and respond to the received requests by processing the received requests using a software application or a combination of software applications. In addition, requests can also be sent to the computer 902 from internal users, external or third-parties, or other entities, individuals, systems, or computers.

Each of the components of the computer 902 can communicate using a network 903 (or system bus). In some implementations, any or all of the components of the computer 902, including hardware, software, or a combination of hardware and software, can interface over the network 903 (or system bus) using an application programming interface (API) 912, a service layer 913, or a combination of the API 912 and service layer 913. The API 912 can include specifications for routines, data structures, and object classes. The API 912 can be either computer-language independent or dependent and refer to a complete interface, a single function, or even a set of APIs. The service layer 913 provides software services to the computer 902 or other components (whether illustrated or not) that are communicably coupled to the computer 902. The functionality of the computer 902 can be accessible for all service consumers using this service layer. Software services, such as those provided by the service layer 913, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 902, alternative implementations can illustrate the API 912 or the service layer 913 as stand-alone components in relation to other components of the computer 902 or other components (whether illustrated or not) that are communicably coupled to the computer 902. Moreover, any or all parts of the API 912 or the service layer 913 can be implemented as a child or a sub-module of another software module, enterprise application, or hardware module without departing from the scope of the present disclosure.

The computer 902 includes an interface 904. Although illustrated as a single interface 904 in FIG. 9, two or more interfaces 904 can be used according to particular needs, desires, or particular implementations of the computer 902. The interface 904 is used by the computer 902 for communicating with another computing system (whether illustrated or not) that is communicatively linked to the network 903 in a distributed environment. Generally, the interface 904 is operable to communicate with the network 903 and comprises logic encoded in software, hardware, or a combination of software and hardware. More specifically, the interface 904 can comprise software supporting one or more communication protocols associated with communications such that the network 903 or interface's hardware is operable to communicate physical signals within and outside of the illustrated computer 902.

The computer 902 includes a processor 905. Although illustrated as a single processor 905 in FIG. 9, two or more processors can be used according to particular needs, desires, or particular implementations of the computer 902. Generally, the processor 905 executes instructions and manipulates data to perform the operations of the computer 902 and any algorithms, methods, functions, processes, flows, and procedures as described in the present disclosure.

The computer 902 also includes a database 906 that can hold data for the computer 902, another component communicatively linked to the network 903 (whether illustrated or not), or a combination of the computer 902 and another component. For example, database 906 can be an in-memory, conventional, or another type of database storing data consistent with the present disclosure. In some implementations, database 906 can be a combination of two or more different database types (for example, a hybrid in-memory and conventional database) according to particular needs, desires, or particular implementations of the computer 902 and the described functionality. Although illustrated as a single database 906 in FIG. 9, two or more databases of similar or differing types can be used according to particular needs, desires, or particular implementations of the computer 902 and the described functionality. While database 906 is illustrated as an integral component of the computer 902, in alternative implementations, database 906 can be external to the computer 902. As illustrated, the database 906 holds the previously described data 916 including, for example, multiple streams of data from various sources, such as measurement data from water salinity measuring probe, the spinner, the fluid holdup probe, the temperature probe, the pressure probe, and the caliper log, as shown in FIGS. 1-3, and 6A-6B.

The computer 902 also includes a memory 907 that can hold data for the computer 902, another component or components communicatively linked to the network 903 (whether illustrated or not), or a combination of the computer 902 and another component. Memory 907 can store any data consistent with the present disclosure. In some implementations, memory 907 can be a combination of two or more different types of memory (for example, a combination of semiconductor and magnetic storage) according to particular needs, desires, or particular implementations of the computer 902 and the described functionality. Although illustrated as a single memory 907 in FIG. 9, two or more memories 907 or similar or differing types can be used according to particular needs, desires, or particular implementations of the computer 902 and the described functionality. While memory 907 is illustrated as an integral component of the computer 902, in alternative implementations, memory 907 can be external to the computer 902.

The application 908 is an algorithmic software engine providing functionality according to particular needs, desires, or particular implementations of the computer 902, particularly with respect to functionality described in the present disclosure. For example, application 908 can serve as one or more components, modules, or applications. Further, although illustrated as a single application 908, the application 908 can be implemented as multiple applications 908 on the computer 902. In addition, although illustrated as integral to the computer 902, in alternative implementations, the application 908 can be external to the computer 902.

The computer 902 can also include a power supply 914. The power supply 914 can include a rechargeable or non-rechargeable battery that can be configured to be either user- or non-user-replaceable. In some implementations, the power supply 914 can include power-conversion or management circuits (including recharging, standby, or another power management functionality). In some implementations, the power-supply 914 can include a power plug to allow the computer 902 to be plugged into a wall socket or another power source to, for example, power the computer 902 or recharge a rechargeable battery.

There can be any number of computers 902 associated with, or external to, a computer system containing computer 902, each computer 902 communicating over network 903. Further, the term "client," "user," or other appropriate terminology can be used interchangeably, as appropriate, without departing from the scope of the present disclosure. Moreover, the present disclosure contemplates that many users can use one computer 902, or that one user can use multiple computers 902.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/−R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used by the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any subcombination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-imple-

What is claimed is:

1. A tool assembly for monitoring reservoir water properties and reservoir production performance at a borehole, the tool assembly comprising:
a water salinity measuring probe that includes a pair of electrodes, wherein the water salinity measuring probe is mounted at a tip of the tool assembly and configured to measure a water conductivity between the pair of electrodes when the tool assembly is immersed inside the borehole, wherein the pair of electrodes are enclosed in a mesh coated with a superhydrophilic material capable of allowing water in and out of the water salinity measuring probe when the tool assembly is immersed inside the borehole;
a spinner tool configured to measure a total flow rate at where the tool assembly is immersed inside the borehole, wherein the spinner tool is located above the water salinity measuring probe when the tool assembly is immersed inside the borehole; and
a temperature probe configured to measure a temperature at where the tool assembly is immersed inside the borehole, wherein the temperature probe is located above the spinner tool when the tool assembly is immersed inside the borehole.

2. The tool assembly of claim 1, wherein the water salinity measuring probe is protected by a water-soluble shell comprising potassium chlorate or magnesium metallic sphere.

3. The tool assembly of claim 1, wherein the pair of electrodes of the water salinity measuring probe are within a predefined distance of each other.

4. The tool assembly of claim 1, further comprising:
a pressure probe configured to measure a pressure at where the tool assembly is immersed inside the borehole.

5. The tool assembly of claim 1, further comprising:
one or more fluid holdup probes co-located with the spinner tool and configured to measure a water holdup, and an oil holdup, when the tool assembly is immersed inside the borehole.

6. The tool assembly of claim 5, further comprising:
a caliper log capable of measuring a diameter of the borehole.

7. The tool assembly of claim 5, wherein the water salinity measuring probe, the spinner tool, the one or more fluid holdup probes, and the temperature probe are coupled to a computer processor, and
wherein the computer processor is configured to:
receive, from the tool assembly, data encoding measured water conductivity, measured total flow rate, measured water holdup, measured oil holdup, and measured temperature when the tool assembly is immersed inside the borehole; and
based on the measured water conductivity and the measured temperature, calculate a flowing water salinity at where the tool assembly is immersed inside the borehole.

8. The tool assembly of claim 7, wherein the tool assembly provides the measured water conductivity, the measured total flow rate, the measured water holdup, the measured oil holdup, and the measured temperature from two or more layers inside the borehole.

9. The tool assembly of claim 8, wherein the computer processor coupled to the tool assembly is further configured to:
receive, for the tool assembly, data encoding measured water conductivity, measured total flow rate, measured water holdup, measured oil holdup, and measured temperature from two or more layers inside the borehole; and
based on the measured water conductivity, the measured total flow rate, the measured water holdup, the measured oil holdup, and the measured temperature from two or more layers inside the borehole, calculate a mixed flowing water salinity inside the borehole.

10. A method for monitoring reservoir production at a borehole, the method comprising:
immersing a tool assembly inside the borehole, wherein the tool assembly includes a water salinity measuring probe, a spinner tool, and a temperature probe, and wherein the water salinity measuring probe includes a pair of electrodes;
operating the pair of electrodes located inside a mesh coated with a superhydrophilic material such that water is allowed in and out of the water salinity measuring probe;
measuring a water conductivity between the pair of electrodes of the water salinity measuring probe when the tool assembly is immersed inside the borehole;
measuring, using the spinner tool of the tool assembly, a total flow rate at where the tool assembly is immersed inside the borehole; and
measuring, using the temperature probe of the tool assembly, a temperature at where the tool assembly is immersed inside the borehole.

11. The method of claim 10, further comprising:
enclosing the water salinity measuring probe with a water-soluble shell comprising potassium chlorate or magnesium metallic sphere.

12. The method of claim 10, further comprising:
mounting the water salinity measuring probe at a tip of the spinner tool.

13. The method of claim 10, further comprising:
measuring, using a pressure probe, a pressure at where the tool assembly is immersed inside the borehole.

14. The method of claim 10, further comprising:
measuring, using one or more fluid holdup probes, a water holdup and an oil holdup when the tool assembly is immersed inside the borehole.

15. The method of claim 14, further comprising:
measuring, using a caliper log, a diameter of the borehole.

16. The method of claim 14, further comprising:
receiving, from the tool assembly, data encoding measured water conductivity, measured total flow rate, measured water holdup, measured oil holdup, and measured temperature when the tool assembly is immersed inside the borehole; and
based on the measured water conductivity and the measured temperature, calculating a flowing water salinity at where the tool assembly is immersed inside the borehole.

17. The method of claim 16, further comprising:
obtaining the measured water conductivity, the measured total flow rate, the measured water holdup, the measured oil holdup, and the measured temperature from two or more layers inside the borehole.

18. The method of claim 17, further comprising:
receiving, for the tool assembly, data encoding measured water conductivity, measured total flow rate, measured water holdup, measured oil holdup, and measured temperature from two or more layers inside the borehole; and based on the measured water conductivity, the measured total flow rate, the measured water holdup, the measured oil holdup, and the measured temperature from two or more layers inside the borehole, calculating a mixed flowing water salinity inside the borehole.

* * * * *